United States Patent [19]

Hoppe et al.

[11] Patent Number: 5,332,813
[45] Date of Patent: Jul. 26, 1994

[54] PROCESS FOR THE CONTINUOUS REACTION OF DIFLUOROTRIAZINYL COMPOUNDS WITH AMINES

[75] Inventors: Manfred Hoppe, Kürten; Wolfgang Müllers, Bergisch Gladbach; Hans-Georg Frosch, Köln; Richard Sommer, Odenthal; Siegbert Arnold, Bonn; Wolfram Reddig, Bergisch Gladbach, all of Fed. Rep. of Germany

[73] Assignee: Bayer Aktiengesellschaft, Leverkusen, Fed. Rep. of Germany

[21] Appl. No.: 971,165

[22] Filed: Nov. 3, 1992

[30] Foreign Application Priority Data

Nov. 13, 1991 [DE] Fed. Rep. of Germany ....... 4137292

[51] Int. Cl.$^5$ .......................................... G07D 251/50
[52] U.S. Cl. .................................... 544/204; 544/113; 544/208; 544/209; 544/210
[58] Field of Search ............... 544/204, 208, 209, 210, 544/113

[56] References Cited

U.S. PATENT DOCUMENTS 4,740,597 4/1988 Franke et al. ...................... 544/211

OTHER PUBLICATIONS

Smolin and Rapoport, *The Chemistry of Heterocyclic Compounds*, "s-Triazines and Derivatives", (1959), p. 55.

H. Zollinger, *Angewandte Chemie*, "Chemismus der Reaktivfarbstoffe", (1961), pp. 125–136.

*Primary Examiner*—John M. Ford
*Attorney, Agent, or Firm*—Sprung Horn Kramer & Woods

[57] ABSTRACT

Difluorotriazinyl compounds of the formula

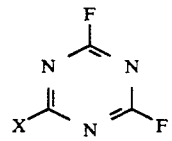

(I)

are continuously reacted in a reactor with amines in solution or suspension.

6 Claims, No Drawings

PROCESS FOR THE CONTINUOUS REACTION OF DIFLUOROTRIAZINYL COMPOUNDS WITH AMINES

The application relates to a process for the continuous reaction of difluorotriazinyl compounds with amines.

The reaction of difluorotriazinyl compounds I

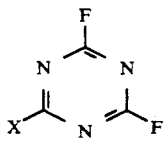

with amines or chromophore-containing amines is carried out by known processes by means of adjusting the temperature and the pH after addition of the components. This is normally performed in stirred vessels, but this entails disadvantages, since, by the addition of one of the components and/or by adjusting the pH, pH gradients and/or stoichiometry gradients are formed.

These disadvantages are caused by the low specific mixing energy in stirred vessels. In the reaction of particularly reactive compounds such as difluorotriazines with amines, these disadvantages lead to yield losses by hydrolysis and side reactions.

The object is to find an improved process for the reaction of triazinyl compounds with amines, in particular aminonaphtholsulphonic acids.

The invention relates to an improved process for the reaction of difluorotriazinyl compounds of the formula I

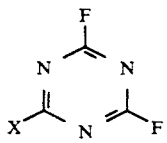

—preferably containing sulphonyl groups—with amines Y-H to give reactive dyes or their precursors of the formula II

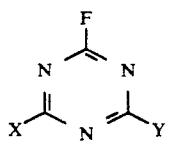

where:

X-H and Y-H are, independently of each other, a primary or secondary aliphatic, aromatic or heterocyclic amine, which can be substituted at one or both radicals of the nitrogen atom, preferably by OH, $OSO_3H$, $SO_3H$, COOH, Cl, $OC_1$-$C_4$-alkyl, $C_1$-$C_4$-alkyl, $SO_2$—$(CH_2)_2$—$OSO_3H$, $SO_2$—CH=$CH_2$, $SO_2$—$(CH_2)_2$—Cl, NH-acyl, NH—$C_1$-$C_4$—alkyl, $CONH(CH_2)_2$—O—$(CH_2)_2$—$SO_2$—CH=$CH_2$, $O(CH_2)_2SO_2$—CH=$CH_2$ or O-acyl, where X-H and/or Y-H can be chromophore-containing amines, characterised in that the difluorotriazinyl compound of type I, as an aqueous or aqueous/organic solution or as a suspension, and the amine Y-H are continuously reacted in a reactor.

Suitable aliphatic and heterocyclic amines X-H or Y-H are, for example, those in which X or Y is a radical of the formula

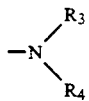

in which $R_3$ = a hydrogen atom or an unsubstituted or substituted lower aliphatic radical or a cycloaliphatic radical and $R_4$ = a hydrogen atom or an unsubstituted or substituted lower aliphatic radical or an unsubstituted or substituted aromatic carbocyclic radical or a lower alkoxy group or the cyano group or the group of the formula —CS—$NH_2$ or an unsubstituted or substituted amino group or $R_3$ and $R_4$, together with the nitrogen atom, form a ring containing a lower alkylene and possibly hetero atoms, such as, for example, a nitrogen or oxygen atom, such as, for example, a morpholine, piperidine or piperazine ring.

Lower aliphatic radicals are in particular lower alkyl and alkenyl radicals.

The expression "lower" used in the above definitions denotes here, as below, that the alkyl or alkylene radical contained in the group comprises 1 to 4 C atoms and the alkenyl radical comprises 2 to 4 C atoms.

Substituted lower alkyl radicals are, for example, alkyl groups of 1 to 4 C atoms, which are substituted by one or two substituents selected from the group comprising acetylamino, hydroxyl, sulphato, $\beta$-sulphatoethylsulphonyl, O—$(CH_2)_2$—$SO_2$—CH=$CH_2$, $\beta$-thiosulphatoethylsulphonyl, lower alkoxy, sulphonyl, carboxyl, phenyl, naphthyl and/or phenyl substituted by sulphonyl, carboxyl, $\beta$-sulphatoethylsulphonyl, $\beta$-thiosulphatoethylsulphonyl, methyl, ethyl, methoxy, ethoxy, chlorine, sulphamoyl, carbamoyl.

Suitable aromatic amines X-H or Y-H are, for example, those of the formula IV

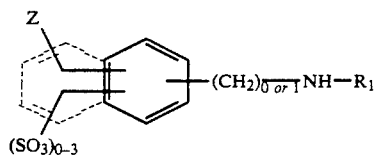

where:

$R_1$ = H, $C_1$-$C_4$-alkyl, which can be substituted by OR, $OSO_3H$, $SO_3H$, COOR or halogen,

R = H, $CH_3$, $C_2H_5$,

Z = H, R, OH, Cl, OR, NH-acyl, NHR, $SO_2$—CH=$CH_2$, $SO_2$—$CH_2$—$CH_2$—$OSO_3H$, O-acyl, or $SO_2$—$CH_2$—$CH_2$—Cl or CONH $(CH_2)_2O(CH_2)_2$—$SO_2$—CH=$CH_2$.

Particularly suitable aromatic amines are, for example:

1-aminobenzene-2-sulphonic acid, 1-aminobenzene-3-sulphonic acid, 1-aminobenzene-4-sulphonic acid, 1-amino-4-methylbenzene-3-sulphonic acid, 1-amino-4-methoxybenzene-3-sulphonic acid, !-amino-2-methylbenzene-4-sulphonic acid, 1-amino-3-methylbenzene-4- sulphonic acid, 1-aminobenzene-3,5-disulphonic acid, 2-amino-5-sulphonylbenzoic acid, 1-aminonaphthalene-4-sulphonic acid, 1-aminonaphthalene-5-sulphonic acid, 1-aminonaphthalene-6-sulphonic acid, 2-aminonaphthalene-5-sulphonic acid, 2-aminonaphthalene-7-sulphonic acid 2-aminonaphthalene-4,8-disulphonic acid, 2-aminonaphthalene-5,7-disulphonic acid, 1,4-diaminobenzene-2,5-disulphonic acid, 1,3-diaminobenzene-4-sulphonic acid, 1,4-diaminobenzene-2-sulphonic acid, 1,3-diaminobenzene-4,6-disulphonic acid, 1-amino-5-hydroxynaphthalene-7-sulphonic acid, 1-amino-8-hydroxynaphthalene-4-sulphonic acid, 1-amino-8-hydroxynaphthalene-3-sulphonic acid, 1-amino-8-hydroxynaphthalene-5-sulphonic acid, 2-amino-5-hydroxynaphthalene-7-sulphonic acid, 2-amino-6-hydroxynaphthalene-8-sulphonic acid, 2-amino-8-hydroxynaphthalene-6-sulphonic acid, 2-methylamino-5-hydroxynaphthalene-7-sulphonic acid, 2-ethylamino-5-hydroxynaphthalene-7-sulphonic acid, 2-methylamino-8-hydroxynaphthalene-6-sulphonic acid, 2-ethylamino-8-hydroxynaphthalene-6-sulphonic acid, 1-amino-6-hydroxynaphthalene-3,8-disulphonic acid, 1-amino-8-hydroxynaphthalene-3,6-disulphonic acid, 1-amino-8-hydroxynaphthalene-2,4-disulphonic acid, 1-amino-8-hydroxynaphthalene-4,6-disulphonic acid, 1-amino-8-hydroxynaphthalene-3,5-disulphonic acid, 2-amino-5-hydroxynaphthalene-7,1-disulphonic acid and 2-amino-8-hydroxynaphthalene-3,6-disulphonic acid.

Aniline-4-$\beta$-sulphatoethyl sulphone, aniline-4-$\beta$-thiosulphatoethyl sulphone, aniline-3-$\beta$-sulphatoethyl sulphone, 2-methoxyaniline-5-$\beta$-thiosulphatoethyl sulphone, 2-methoxyaniline-5-$\beta$-thiosulphatoethyl sulphone, 4-methoxyaniline-3-$\beta$-sulphatoethyl sulphone, 2,5-dimethoxyaniline-4-$\beta$-sulphatoethyl sulphone, 2,5-dimethoxyaniline-4-$\beta$-sulphatoethyl sulphone, 2-methoxy-5-methylaniline-4-$\beta$-sulphatoethyl sulphone, aniline-2-$\beta$-sulphatoethyl sulphone, 2-chloroaniline-5-$\beta$-sulphatoethyl sulphonne, 4-chloroaniline-3-$\beta$-sulphatoethyl sulphone, 3-(3- or 4-aminobenzoyl)-aminophenyl-$\beta$-sulphatoethyl sulphone, 6-carboxyaniline-3-vinyl sulphone, 2-sulphonylaniline-4-$\beta$-sulphatoethyl sulphone, 2-sulphonylaniline-4-vinyl sulphone, 2,4-disulphonylaniline-5-vinyl sulphone, 2-hydroxyaniline-5-$\beta$-sulphatoethyl sulphone, 2-hydroxyaniline-4-$\beta$-sulphatoethyl sulphone, 3-sulphonyl-2-hydroxyaniline-5-$\beta$-sulphatoethyl sulphone, 2-naphthylamine-8-$\beta$-sulphatoethyl sulphone, 2-naphthylamine-6-$\beta$-sulphatoethyl sulphone, 1-sulphonyl-2-naphthylamine-6-$\beta$-sulphatoethyl sulphone, 1-naphthylamine-4-$\beta$-sulphatoethylsulphone, 1-sulphonyl-2-naphthylamine-5-$\beta$-sulphatoethyl sulphone, 6-sulphonyl-2-naphthylamine-8-$\beta$-sulphatoethyl sulphone, 2-amino-3-sulphonylnaphthalene-6,8-bis-($\beta$-sulphatoethyl sulphone), N-methylaniline, N-ethylaniline, N-$\beta$-hydroxyethylaniline, N-$\beta$-sulphatoethylaniline, 3-aminobenzoic acid, 4-aminobenzoic acid, aniline, 3-chloroaniline and 4-chloroaniline.

Chromophore-containing amines Y-H and/or X-H which are considered are, in particular, dyes of the following structural types:

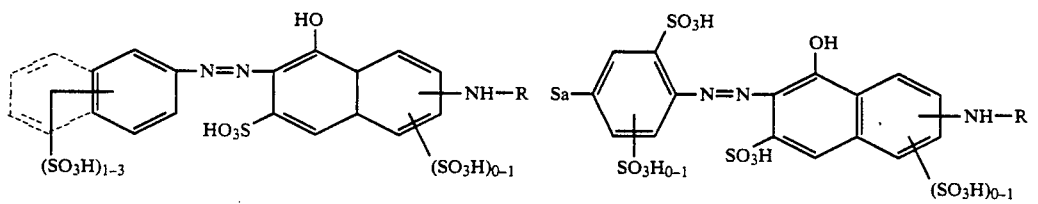

Where Sa = $H_5C_2-O-$ or $H_3C-O-$

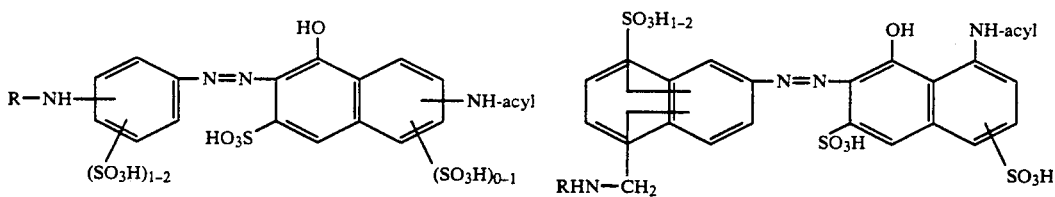

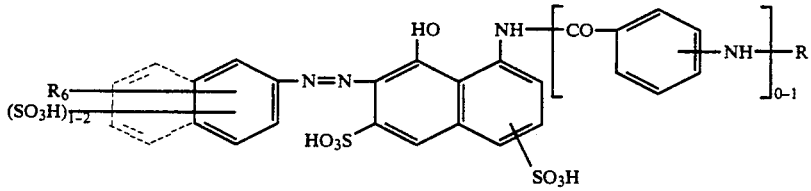

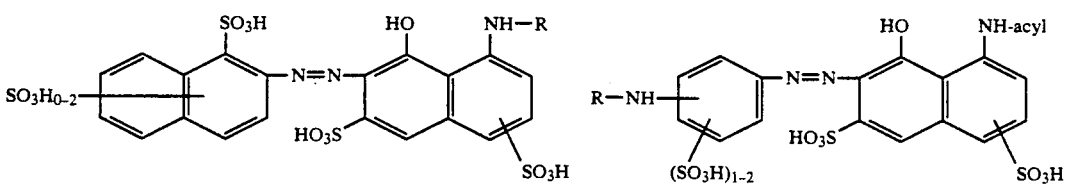

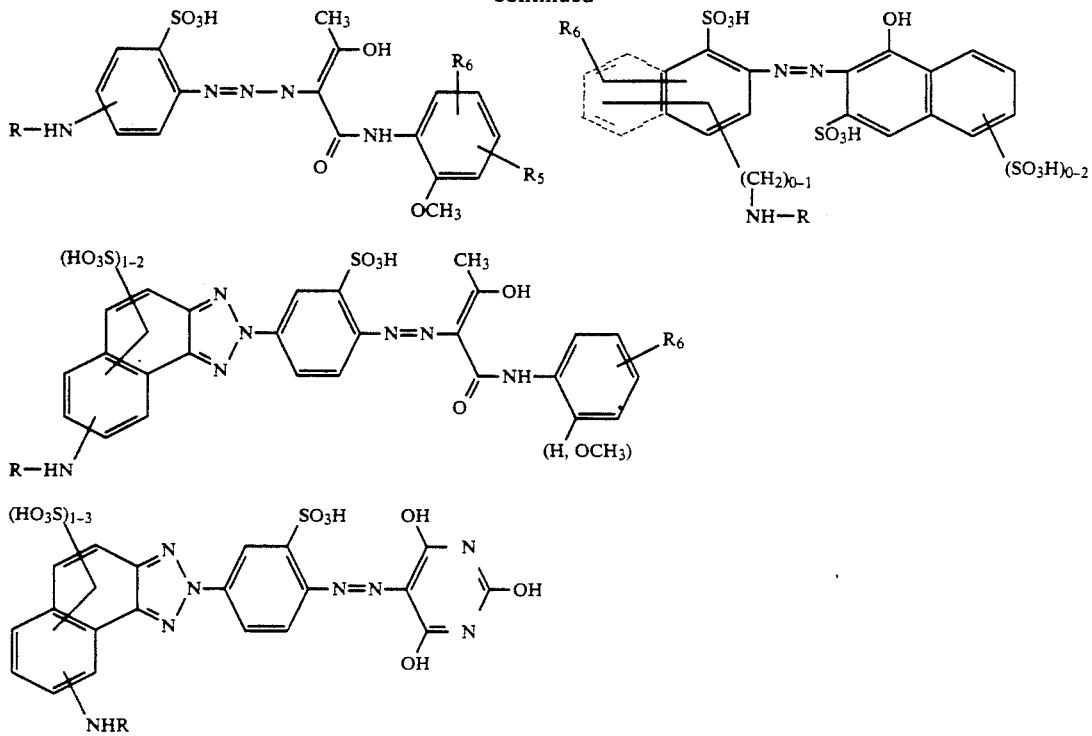
in which
acyl is, for example, acetyl or unsubstituted or substituted benzoyl,
$R_6$ = H, $C_1$-$C_4$-alkyl, $C_1$-$C_4$-alkoxy, Cl, Br, COOH or $SO_3H$.
Metal complexes of dyes of the formulae:
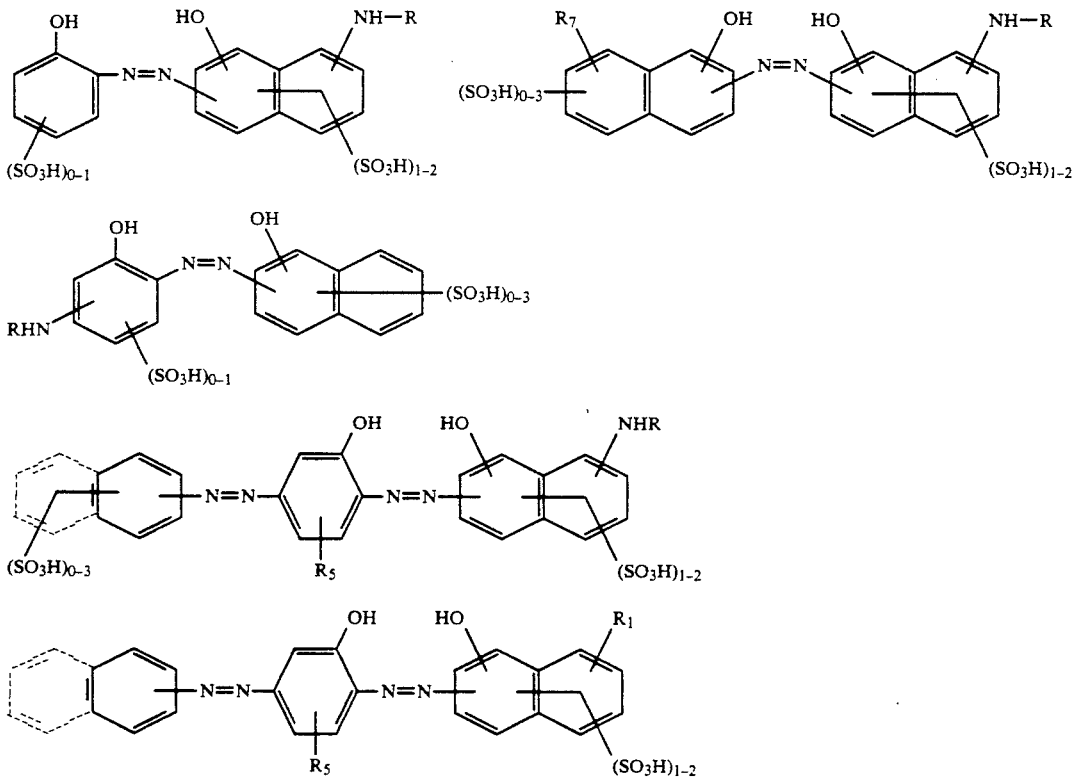
R = H, $CH_3$ or $C_2H_5$,
$R_1$ has the abovementioned meaning,
$R_5$ = H, $CH_3$, $OCH_3$ or Cl,
in which
$R_7$ = H, OH, $NH_2$, $NHCOCH_3$, NHCOPh, Cl, $C_1$-$C_4$-alkoxy or $C_1$-$C_4$-alkyl.

The metal atom preferred is Cu (1:1 complex) or Cr and Co (1:2 complex). Cr and Co complexes can contain, once or twice, the azo compound of the formula given above, that is to say they can be formed symmetrically or unsymmetrically with any other ligand groups.
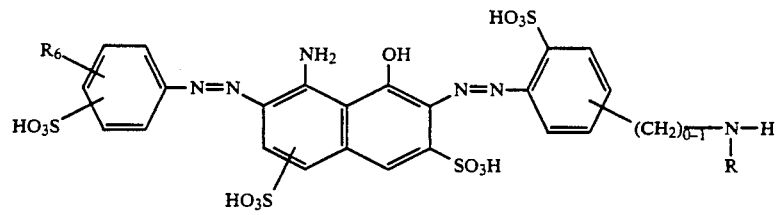
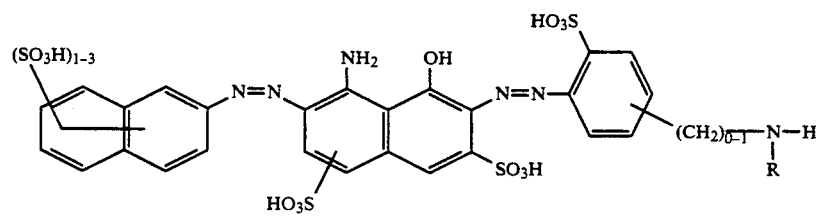
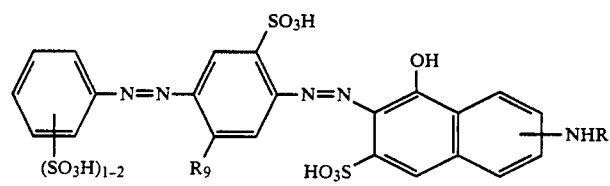
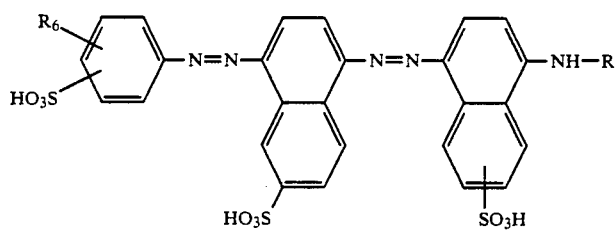
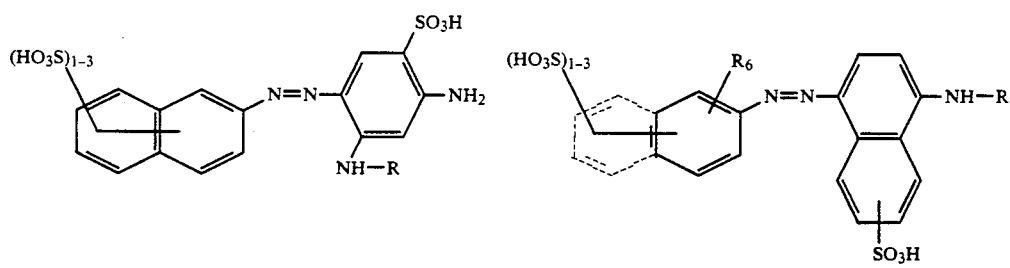
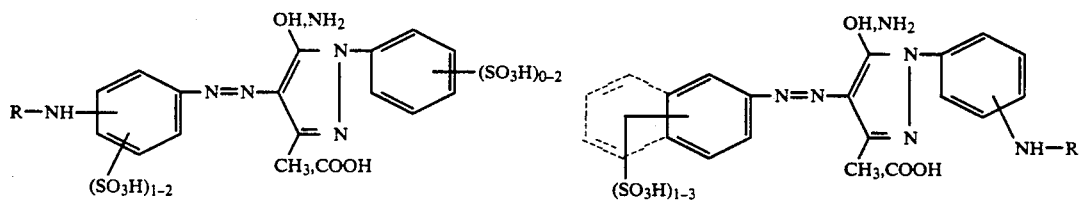
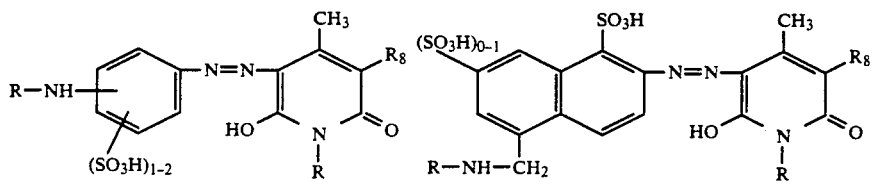

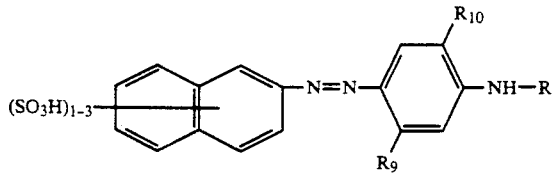

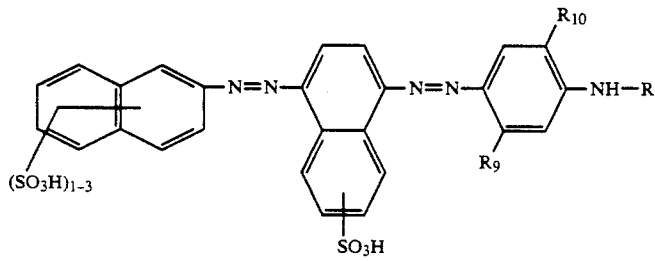

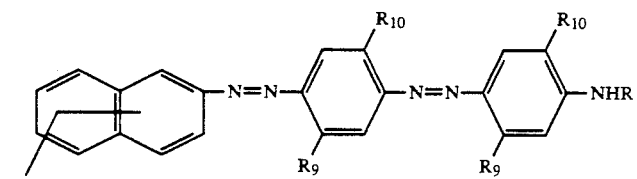

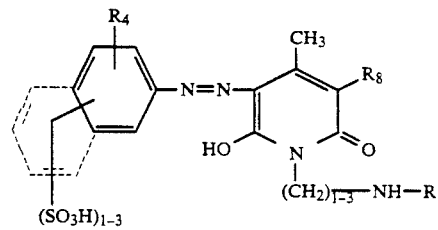

in which
$R_8$=H, $SO_3H$, $CH_2SO_3H$, Cl, $C_1$-$C_4$-alkylsulphonyl, CN, carbonamide, in particular $CONH_2$,
$R_9$=H, $C_1$-$C_4$-alkyl, $C_1$-$C_4$-alkoxy, acylamino, in particular $C_1$-$C_4$-calkylcarbonylamino or arylcarbonylamino such as unsubstituted or substituted phenylcarbonylamino, $C_1$-$C_4$-alkylsulphonylamino, Cl, Br, aminocarbonylamino, $C_1$-$C_4$-alkylsulphonylamino, arylsulphonylamino,
$R_{10}$=H, $C_1$-$C_4$-alkyl, $C_1$-$C_4$-alkoxy, OH or $SO_3H$.

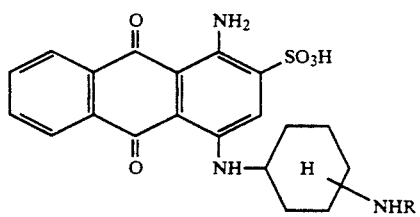

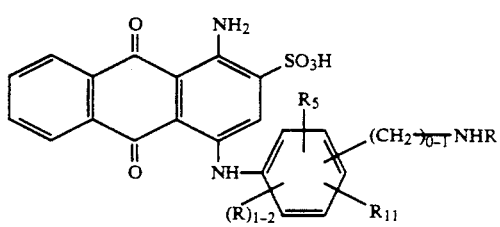

in which
$R_5$=H, methyl, methoxy, chlorine
$R_{11}$=H, $SO_3H$ and
R=H, methyl or ethyl.

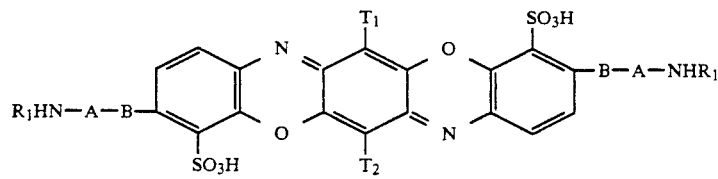

in which
A represents an unsubstituted or substituted phenylene or an unsubstituted or substituted aromatic-aliphatic bridge member or a straight-chain or branched $C_1$-$C_6$-alkylene, uninterrupted or interrupted by hereto atoms such as groups containing NR, O or S, which alkylene can be substituted by OR, $OSO_3H$, $SO_3H$, COOR or halogen.

Within a bridge member A, NR, with $NR_1$ or $NR_2$, can alternatively form a heterocyclic aliphatic ring.

$$B = \underset{\underset{R_1}{|}}{N}, O \text{ and}$$

$T_1$, $R_2$=H, Cl, Br, $C_1$-$C_2$-alkyl, $OCH_3$, $OC_2H_5$, acylamino or $C_1$-$C_2$-alkoxycarbonyl.

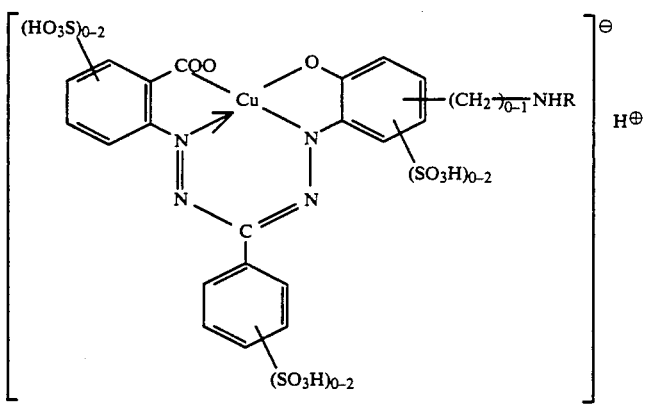
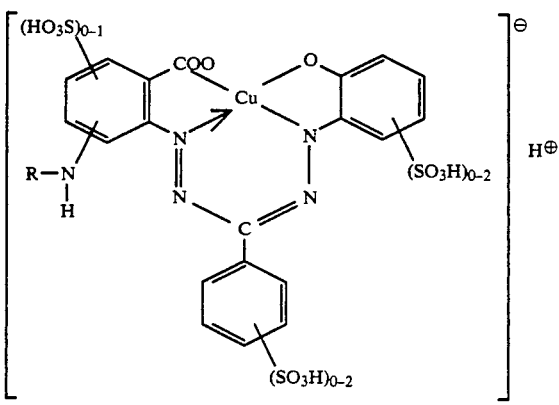
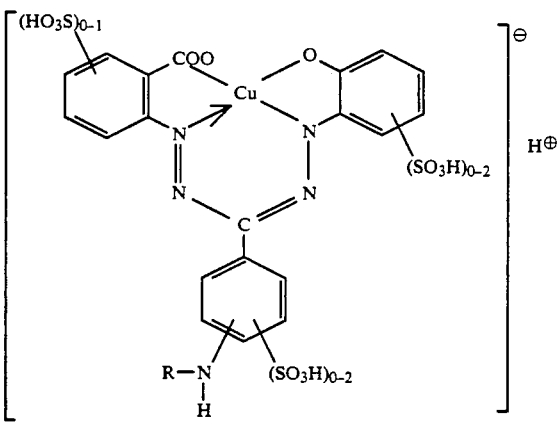
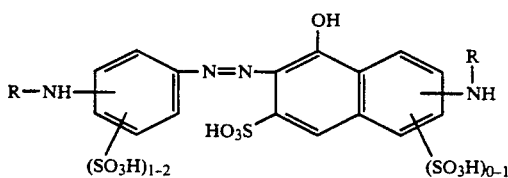
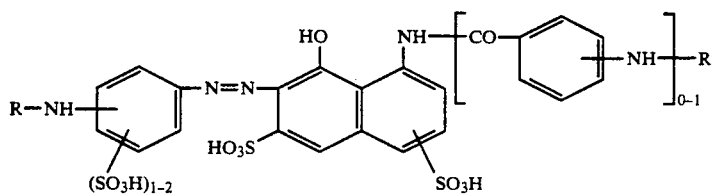

-continued
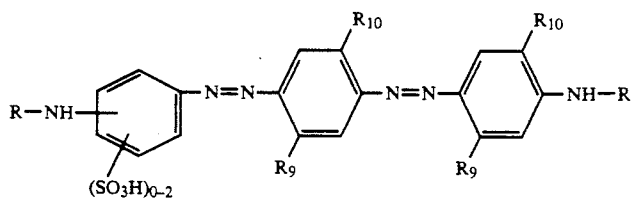
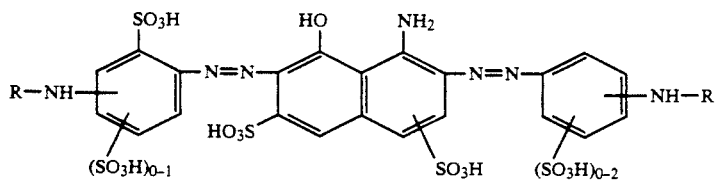
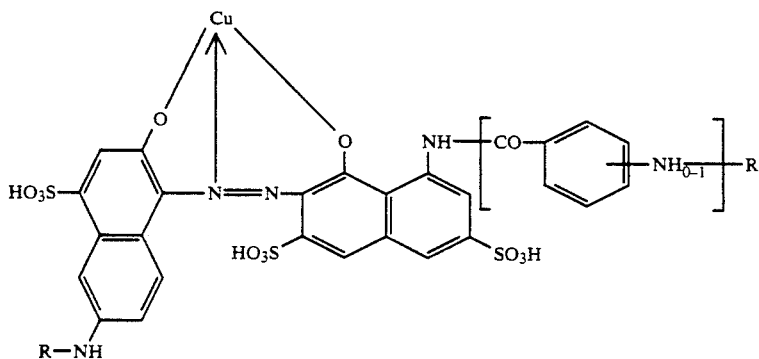
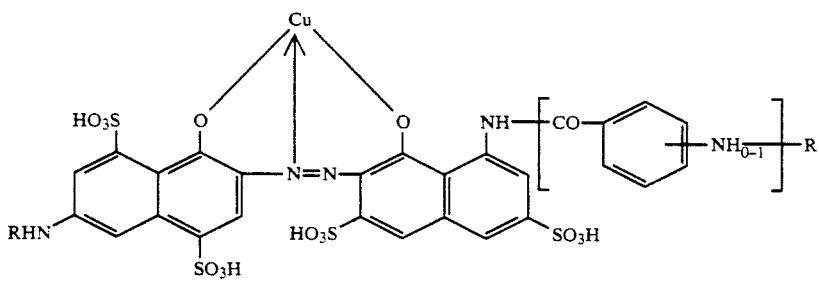
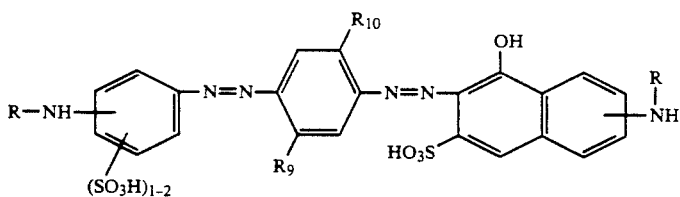
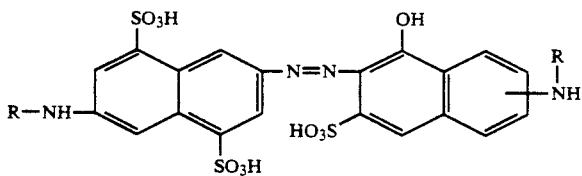
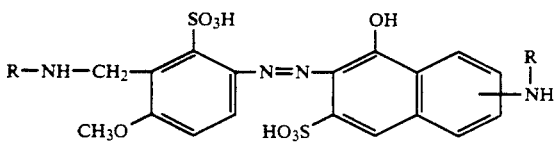

-continued
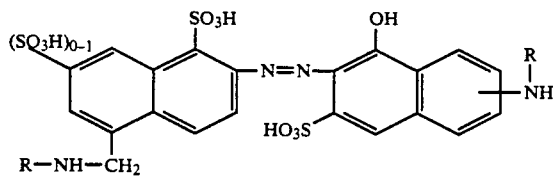
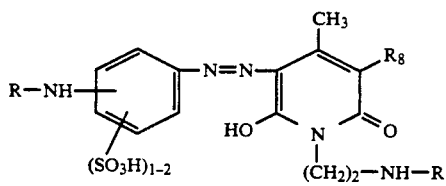
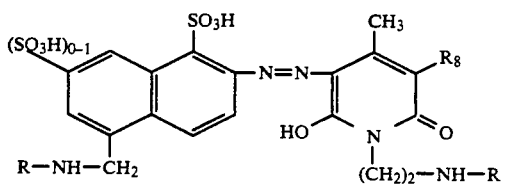
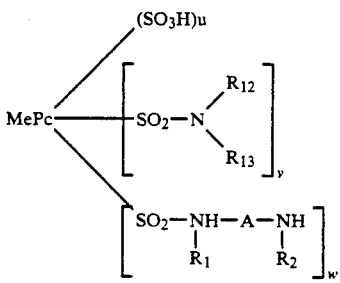
in which
Me=Cu or Ni,
u+v+w=3.4–4.0, with the proviso that
u=0.8–2.0,
v=0–1.0,
w=1.0–3.0 and
$R_1$ and A have the meanings given above,
$R_{12}$ and $R_{13}$=H or $C_1$-$C_2$-alkyl, unsubstituted or substituted by OH, $OSO_3H$, $SO_3H$ or COOH.
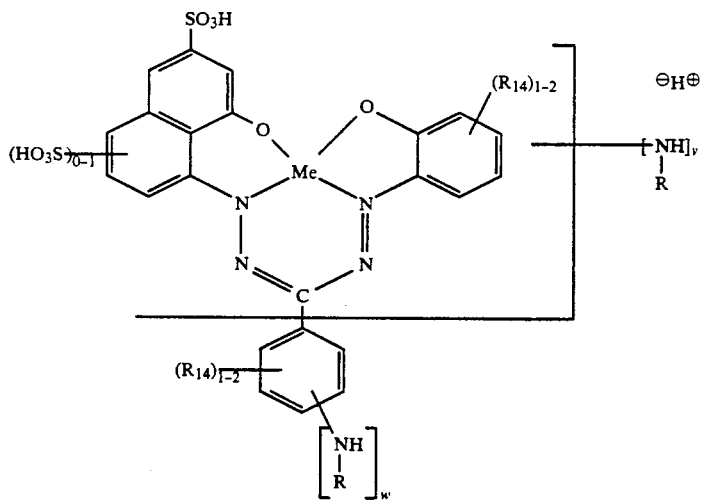
v, w=0 or 1, where w is not equal to v,

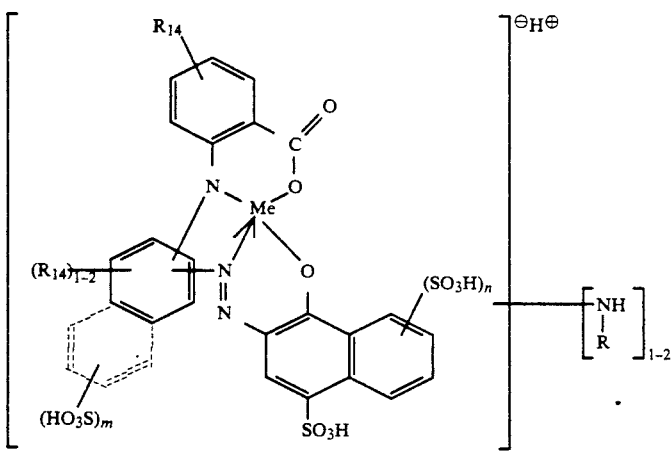

$R_{14}$=H, $C_1$–$C_4$-alkyl, $C_1$-$C_4$-alkoxy, OH, halogen, COOH, $NO_2$, $SO_3H$, sulphonamido, $C_1$-$C_4$-alkylcarbonylamino, unsubstituted or substituted phenylcarbonylamino, $C_1$-$C_4$-alkylsulphonylamino, unsubstituted or substituted phenylsulphonylamino, Me=a divalent metal atom, preferably Fe, Cu, Zn, Co or Ni, being selected so that a considerable conversion is achieved in the reactor.

Suitable reactors are, for example, Jet reactors as described by Zehner, P. and Bittins, K.: Fortschr. Verf. Technik D 23, 1985; p. 373-393, in which the starting materials are simultaneously and continuously introduced into the reactor at different velocities and inten-

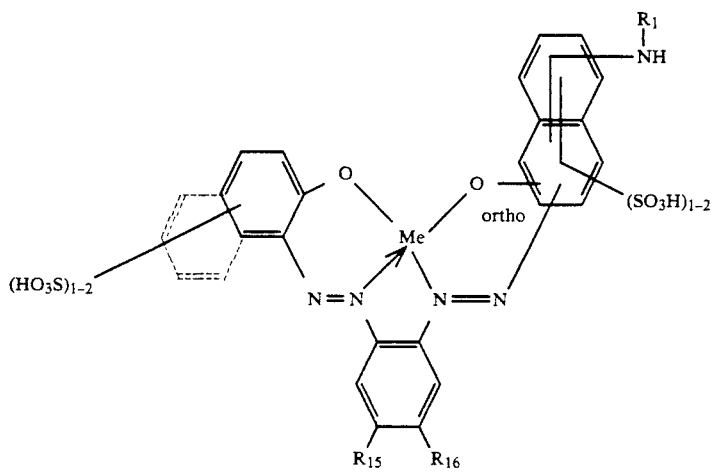

in which $R_{15}$=$C_1$-$C_4$-alkyl, halogen, in particular chlorine, $C_1$-$C_4$-alkoxy, $C_1$-$C_4$-alkylcarbonylamino, arylcarbonylamino or aralkylcarbonylamino, $R_{16}$=$C_1$-$C_4$-alkoxy, or $R_{15}$ and $R_{16}$ form a ring and have the meaning below:

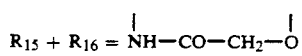

or

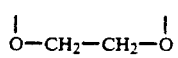

Suitable reactors are those in which the reactants are intensively mixed together in the stoichiometrically desired ratio with high specific energy input and with avoidance or at least minimisation of back-mixing, the reaction conditions, for example temperature and pH, sive mixing is effected by means of the difference in the flow velocities, and the reaction in this case, with flow being substantially free from back-mixing, is to a considerable extent concluded in this reactor. Suitable reactors are also in particular those of the type given in FIG. 1 of DE-A-40 16 159.

Further suitable reactors are dispersion units of the rotor/stator mixer type (O. Fuchs, Chemiker-Zeitung - Chem. Apparatur 84, Jahrgang (1960), No. 24, p. 809 ff), which achieved a very intensive mixing by means of high rotary speeds and small reaction volumes.

The following process variants are preferred with use of the reactors according to the invention:

A solution or suspension of I and a solution or suspension of Y-H are simultaneously and continuously fed to the reactor by separate feeds. The base required for exact adjustment of the pH in the reactor is previously added to one or both starting materials. The adjustment of the stoichiometry is performed by controlling the streams of starting materials and the temperature is controlled by cooling or heating one or both starting materials.

A mixture of I and Y-H, the stoichiometric relationship of which has been previously established, is fed to the reactor as a solution or a suspension at a controlled temperature. Simultaneously and continuously, via a separate feed, the amount of base required to attain the reaction pH is conveyed into the reactor - if required, at a controlled temperature.

A solution or suspension of I and Y-H are fed to the reactor simultaneously and continuously via separate feeds - if required, at a controlled temperature. The amount of base required for the reaction is conveyed simultaneously and continuously into the reactor via a third feeder—if required, at a controlled temperature.

These process variants enable an optimal adjustment of the condensation conditions of I with the amine Y-H, with respect to stoichiometry, pH and temperature, to the requirements of the starting materials, the reaction kinetics and the reaction product II.

An advantage of the process is the substantial avoidance of by-products and secondary products. This is possible by means of the intensive mixing in a short period of time, the precise control of the process parameters and the avoidance or minimisation of back-mixing.

The residence time in the reactor is sufficient for the conversion already to have been carried out to a considerable extent.

To complete the reaction, further continuous-flow reactors such as, for example, rotor/stator systems, a flow tube possibly equipped with a static mixer and stirred vessels can be used. Alternatively, the reaction can also be completed in discontinuously stirred vessels.

The feeding of the components I, amine Y-H and base into the reactor is carried out for example centrally and via a concentric annular gap (jet reactor) or centrally and into one or more of the rotor rings (rotor/stator mixer).

According to a further particular embodiment of the novel process, the reaction is carried out at temperatures of 0° to 90° C., preferably 0° to 50° C.

The amount of alkali in the amine solution is selected so that towards the end of the reaction, a pH between 4 and 11, preferably between 5 and 10, is established.

If a chromophore-containing amine Y-H is reacted with a difluorotriazinyl compound I, the reactive dye obtained can be isolated or can be dried directly without intermediate isolation.

In the reaction of I with a non-chromophore-containing amine, the reaction product can be isolated, but it is preferably further processed without intermediate isolation, for example to give reactive dyes, either by subsequent diazotisation and coupling with a coupling component or by reaction with diazotisation.

This further processing can be carried out discontinuously or continuously in a known manner.

By use of the process according to the invention, the condensation products of the difluorotriazinyl compound I and amines are obtained in many cases in significantly higher purity than by using the hitherto conventional processes. This improves the quality of the reactive dyes prepared from the condensation products, since the condensation products are conventionally further processed without intermediate purification.

EXAMPLE 1

In a Jet nozzle reactor having a volume of 60 cm³, there are fed, simultaneously and continuously via two separate feeds, 40 l/h of sodium carbonate solution (200 g/l) at 20° C., centrally, and also 38 l/h of an aqueous solution (pH=4; 0° C.) of 0.45 mol/l of morpholine and 0.45 mol/l of the compound (1) of the formula

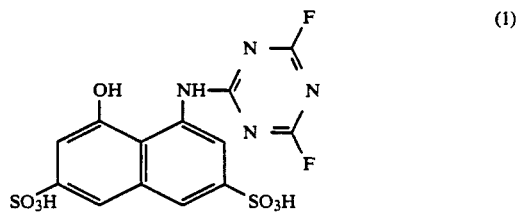

through an annular gap, in such a manner that the sodium carbonate solution enters into the flowing aqueous solution of 1 and morpholine with a pressure drop of 34 bar and back-mixing is substantially avoided in the reactor.

The reaction mixture, which leaves the reactor at a temperature of 20° to 21° C. and with a pH of 8.5 to 8.6, contains the compound of the formula (2),

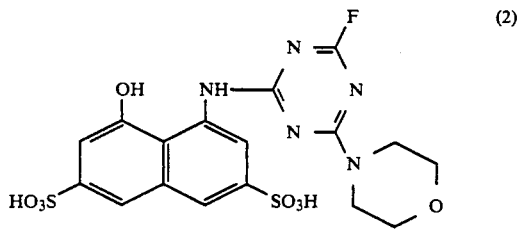

the conversion following the reactor being over 95% and (2) being obtained in very high purity.

(2) is reacted with the diazonium salt of 2-naphthylamine-2-sulphonic acid by known methods. The reactive dye of the formula

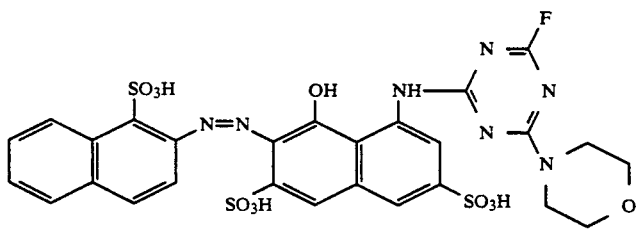

is obtained, which dyes cellulose material in red shades.

EXAMPLE 2

If, instead of morpholine, analogous amounts of aniline are used and the solution of (1) and aniline is fed centrally with a pressure drop of 30 bar and the sodium carbonate solution is fed via the annular gap and the procedure analogous to Example 1 is otherwise followed, the dye of the formula

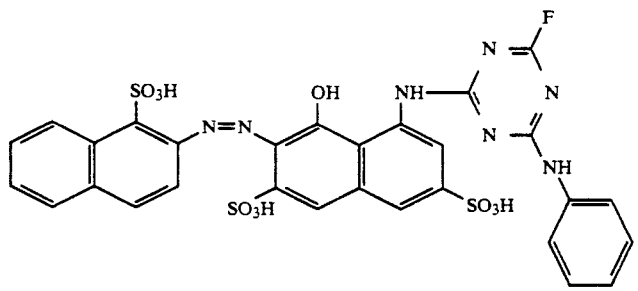

is obtained, which dyes cellulose materials in clear red shades.

EXAMPLE 3

Into a dispersion unit of the rotor/stator mixer type, there are passed in centrally, simulttaneously and conntinuously 50.0 kg/h of a homogeneous cold, 10° C., suspension of $Na_2CO_3$ in water (167 g/l) and, into one of the rotor rings, 33.6 kg/h of a solution of 0.45 mol/l of (1) and 0.45 mol/l of morpholine (pH=4.0; 0° C.).

The reaction mixture, which leaves the reactor at a temperature of approximately 15° C. and a pH of 9.0 to 9.2, contains the compound of the formula (2),

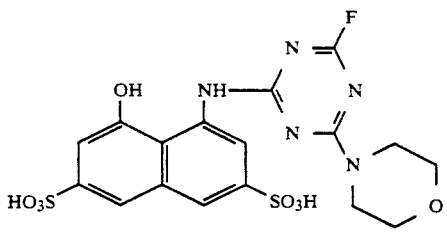 (2)

he conversion following the reactor being over 90% and (2) being obtained in very high purity.

(2) is reacted with the diazonium salt of 2-naphthylamine- 1,5-disulphonic acid by known processes. The reactive dye of the formula

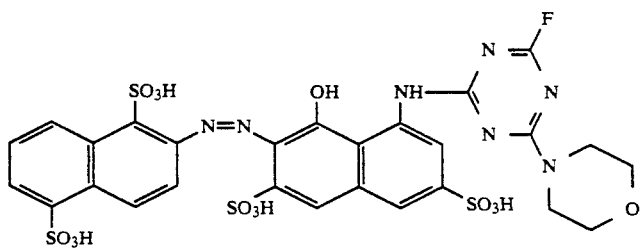

is obtained, which dyes cellulose material in red shades.

EXAMPLE 4

Into a dispersion unit of the rotor/stator mixer type, there are fed centrally, simultaneously and continuously via two separate feeds 33.6 kg/h of a solution of (1) (0.45 mol/l, pH 4, 0° C.) and 30 l/h of a solution of N-ethylaniline in water (0.45 mol/l, pH 4, 0° C.) to one of the rotor rings and 50 kg/h of a cold, 10° C., suspension of $Na_2CO_3$ in water (167 g/l) to the other rotor ring. The reaction mixture which leaves the reactor contains the compound of the formula

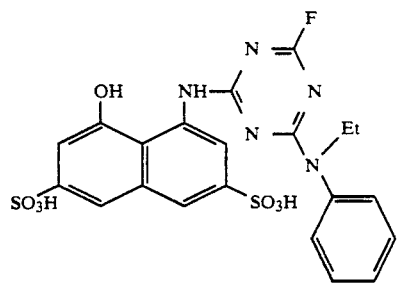

which, analogously to Example 3, is converted to the dye of the formula

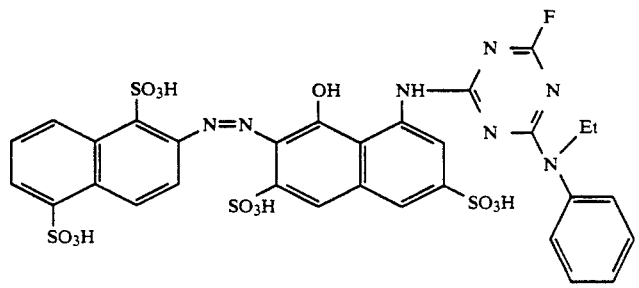

which dyes cotton in clear red shades.

EXAMPLE 5

Into a dispersion unit of the rotor/stator mixer type, there are conducted centrally, simultaneously and continuously via separate feeds 23 l/h of a solution of (3)

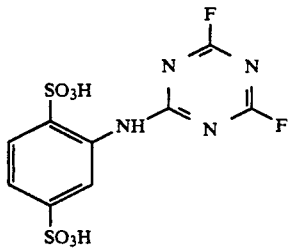
(3)

(0.29 mol/l; pH 3; 0° C.) and 38.3 kg/h of a solution of (4) (0.1 mol/l, pH>13, 10° C.) to one of the rotor discs.

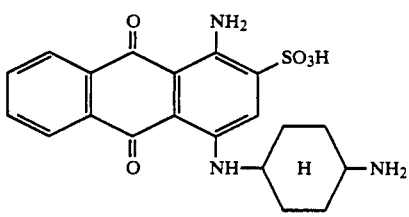
(4)

The reaction mixture which leaves the reactor (pH 8.5; 19° C.) contains the reactive dye of the formula

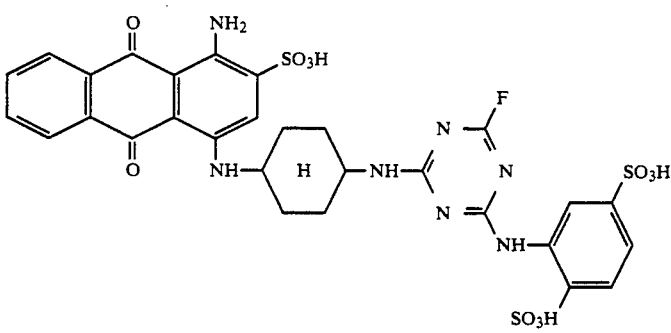
(5)

the conversion to (5) following the reactor being more than 60%. The reaction is completed in a residence time section or in one or more stirred vessels.

We claim:

1. A process for the preparation of a compound of the formula

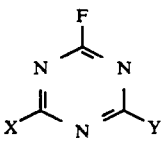
(II)

in which X and Y each independently is
i)

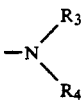

in which $R_3$ is a hydrogen atom or an optionally substituted $C_1$-$C_4$ aliphatic radical and $R_4$ is a hydrogen atom, optionally substituted $C_1$-$C_4$ aliphatic radical or $C_1$-$C_4$ alkoxy group, cyano or an amino group, at least one of $R_3$ and $R_4$ not being hydrogen and carrying as a substituent at least one member selected from the group consisting of acetylamino, hydroxyl, sulphato, β-sulphatoethyl-sulphonyl, O—(CH$_2$-)$_2$—SO$_2$—CH=CH$_2$, β-thiosulphatoethyl-sulphonyl, lower alkoxy, sulpho, carboxyl, phenyl, naphthyl or phenyl substituted by sulpho, carboxyl, β-sulphatoethylsulphonyl, β-thiosulphatoethylsulphonyl, methyl, ethyl, methoxy, ethoxy, chlorine, sulphamoyl and carbamoyl, or ii)

in which $R_3$ and $R_4$, together with the nitrogen atom, form a morpholine, piperidine or piperazine ring, or iii) an amine radical of the formula

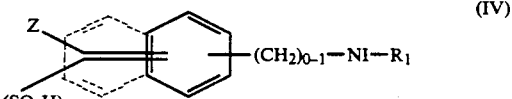
(IV)

in which $R_1$ is H or $C_1$-$C_4$-alkyl optionally substituted by OR, OSO$_3$H, SO$_3$H, COOR or halogen, R is H, CH$_3$ or C$_2$H$_5$, and Z is H, R, OH, Cl, OR, NH-acyl, NHR, SO$_2$—CH=CH$_2$, SO$_2$—CH$_2$—CH$_2$—OSO$_3$H, SO$_2$—CH$_2$—CH$_2$—Cl, CONH(CH$_2$)$_2$O(CH$_2$)$_2$—SO$_2$—CH=CH$_2$ or O-acyl, or iv) a chromophore-containing amine, which comprises continuously reacting a difluorotriazinyl compound of the formula

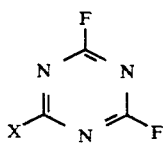

(I)

in an aqueous or aqueous/organic solution or in suspension, with an amine of the formula

Y—H the starting materials being passed simultaneously and continuously into a 1) reactor at different velocities and achieving intensive mixing by means of the difference in flow velocities, or
2) rotor/stator mixer and achieving highly intensive mixing therein in a short period of time as a result of the high rotary speed and the small reaction volume, the reaction being carried out with substantially no backmixing.

2. A process according to claim 1, wherein the reaction is effected in a rotor/stator mixer or a jet reactor.

3. A process according to claim 1, wherein the starting material I is of the formula

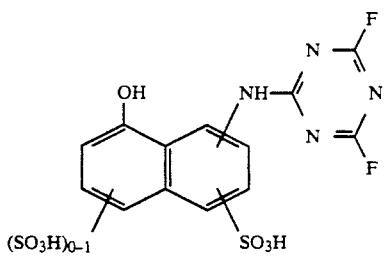

4. A process according to claim 1, wherein the starting material I is of the formula

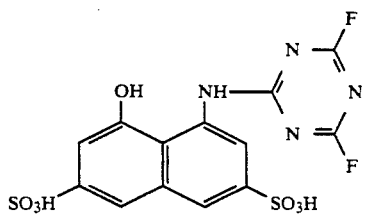

and is reacted with morpholine.

5. A process according to claim 1, wherein the starting materials are passed simultaneously and continuously at different velocities into a reactor, and intensive mixing is achieved by means of the difference in the flow velocities.

6. A process according to claim 1, wherein the starting materials are passed simultaneously and continuously into a rotor/stator mixer and are highly intensively mixed therein in a short period of time as a result of the high rotary speed and the small reaction volume.

* * * * *